United States Patent
Raju et al.

(10) Patent No.: US 11,166,666 B2
(45) Date of Patent: Nov. 9, 2021

(54) ENHANCED ACUTE CARE MANAGEMENT COMBINING IMAGING AND PHYSIOLOGICAL MONITORING

(71) Applicant: KONINKLIJKE PHILIPS N.V., Eindhoven (NL)

(72) Inventors: Balasundar Iyyavu Raju, North Andover, MA (US); Nicolas Wadih Chbat, White Plains, NY (US); Emil George Radulescu, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 322 days.

(21) Appl. No.: 15/765,291

(22) PCT Filed: Oct. 7, 2016

(86) PCT No.: PCT/IB2016/056025
§ 371 (c)(1),
(2) Date: Apr. 2, 2018

(87) PCT Pub. No.: WO2017/060871
PCT Pub. Date: Apr. 13, 2017

(65) Prior Publication Data
US 2018/0286518 A1    Oct. 4, 2018

Related U.S. Application Data

(60) Provisional application No. 62/239,308, filed on Oct. 9, 2015.

(51) Int. Cl.
*A61B 5/00*    (2006.01)
*A61M 16/00*   (2006.01)
(Continued)

(52) U.S. Cl.
CPC .......... *A61B 5/4836* (2013.01); *A61B 5/0205* (2013.01); *A61B 5/02007* (2013.01);
(Continued)

(58) Field of Classification Search
CPC .... G16H 50/50; G16H 50/30; A61B 5/02007; A61B 5/02055; A61B 5/1128;
(Continued)

(56) References Cited

U.S. PATENT DOCUMENTS 5,931,160 A * 8/1999 Gilmore ............ A61M 16/0051
                                                  128/204.21
10,702,166 B1 * 7/2020 Freeman .................. A61B 5/08
(Continued)

FOREIGN PATENT DOCUMENTS

JP         2007044364 A      2/2007

OTHER PUBLICATIONS

Chbat et al.: "A Comprehensive Cardiopulmonary Simulation Model for the Analysis of Hypercapnic Respiratory Failure"; 31st Annual International Conference of the IEEE EMS, Sep. 2009, pp. 5474-5477.
(Continued)

*Primary Examiner* — Carl H Layno
*Assistant Examiner* — Manolis Pahakis

(57) ABSTRACT

A patient monitoring device includes at least one physiological sensor (32) configured to acquire at least one measured value for a patient of at least one monitored physiological variable. A cardiovascular (CV), pulmonary, or cardiopulmonary (CP) modeling component (42) includes a microprocessor pro-programmed to: receive the measured values of the at least one monitored physiological variable; receive a value for at least one patient-specific medical image parameter generated from at least one medical image of the patient; compute values for the patient of unmonitored
(Continued)

physiological variables based on the measured values for the patient of the monitored physiological variables and the patient-specific medical image parameter; and at least one of (1) display the computed values and (2) control a therapy device delivering therapy to the patient based on the computed values.

16 Claims, 2 Drawing Sheets

(51) Int. Cl.

| | |
|---|---|
| G16H 40/63 | (2018.01) |
| G16H 50/30 | (2018.01) |
| G16H 30/40 | (2018.01) |
| G16H 50/50 | (2018.01) |
| A61B 5/02 | (2006.01) |
| A61B 5/0205 | (2006.01) |
| A61B 5/11 | (2006.01) |
| G16B 5/00 | (2019.01) |
| A61B 8/06 | (2006.01) |
| A61B 5/318 | (2021.01) |
| A61B 5/145 | (2006.01) |
| A61B 5/08 | (2006.01) |

(52) U.S. Cl.
CPC ........ *A61B 5/02055* (2013.01); *A61B 5/1128* (2013.01); *A61B 5/4848* (2013.01); *A61M 16/024* (2017.08); *A61M 16/026* (2017.08); *G16H 30/40* (2018.01); *G16H 40/63* (2018.01); *G16H 50/30* (2018.01); *G16H 50/50* (2018.01); *A61B 5/14542* (2013.01); *A61B 5/318* (2021.01); *A61B 8/065* (2013.01); *A61B 2505/03* (2013.01); *A61B 2576/023* (2013.01); *A61M 2205/505* (2013.01); *A61M 2205/581* (2013.01); *A61M 2205/583* (2013.01); *A61M 2230/005* (2013.01); *A61M 2230/04* (2013.01); *A61M 2230/205* (2013.01); *A61M 2230/30* (2013.01); *A61M 2230/432* (2013.01); *A61M 2230/435* (2013.01); *G16B 5/00* (2019.02)

(58) Field of Classification Search
CPC ... A61B 5/4836; A61B 5/4848; A61B 5/0402; A61B 5/14542; A61M 2205/505; A61M 2205/581; A61M 2205/583; A61M 2230/04; A61M 2230/205; A61M 2230/30; A61M 2230/432; A61M 2230/435
See application file for complete search history.

(56) References Cited

U.S. PATENT DOCUMENTS

| | | | |
|---|---|---|---|
| 2008/0202527 A1* | 8/2008 | Hutchinson | A61M 16/024 128/204.23 |
| 2008/0214961 A1 | 9/2008 | Matsumoto et al. | |
| 2009/0120435 A1* | 5/2009 | Slessarev | A61M 16/08 128/203.14 |
| 2010/0056931 A1 | 3/2010 | Soffer et al. | |
| 2011/0144517 A1* | 6/2011 | Cervantes | A61B 5/0873 600/538 |
| 2011/0315147 A1* | 12/2011 | Wood | A61M 16/042 128/207.15 |
| 2013/0006094 A1* | 1/2013 | Charles | A61B 5/7285 600/411 |
| 2013/0079658 A1* | 3/2013 | Cardoso | A61B 5/0059 600/532 |
| 2013/0116555 A1* | 5/2013 | Kuzelka | A61M 16/024 600/427 |
| 2013/0125883 A1* | 5/2013 | Bonassa | A61M 16/0057 128/202.22 |
| 2013/0225978 A1* | 8/2013 | Remmele | G01R 33/5608 600/420 |
| 2014/0053837 A1* | 2/2014 | Klein | A61M 16/20 128/203.14 |
| 2014/0058715 A1* | 2/2014 | Sharma | A61B 5/02007 703/11 |
| 2014/0066749 A1* | 3/2014 | Dickerson | A61B 5/4836 600/413 |
| 2014/0230818 A1* | 8/2014 | Jafari | A61M 16/026 128/204.23 |
| 2014/0366878 A1* | 12/2014 | Baron | A61B 5/4836 128/204.23 |
| 2015/0040905 A1* | 2/2015 | Kulstad | A61M 16/0051 128/204.23 |
| 2015/0290418 A1* | 10/2015 | Kaczka | A61M 16/18 128/200.14 |
| 2016/0008561 A1* | 1/2016 | Novotni | A61B 5/0536 128/204.23 |
| 2016/0029973 A1* | 2/2016 | Kahlman | A61B 5/015 600/301 |
| 2016/0245830 A1* | 8/2016 | Mace | G16H 40/40 |
| 2016/0360996 A1* | 12/2016 | Smith | A61B 5/0816 |
| 2018/0235473 A1* | 8/2018 | Meftah | A61B 5/02416 |
| 2018/0286518 A1* | 10/2018 | Raju | G16H 50/50 |
| 2019/0087955 A1 | 3/2019 | Takahashi et al. | |
| 2019/0175057 A1* | 6/2019 | Krimsky | A61B 5/062 |
| 2020/0038609 A1* | 2/2020 | Wolf | A61B 8/4227 |
| 2021/0016035 A1* | 1/2021 | Euliano, II | A61M 16/024 |
| 2021/0146072 A1* | 5/2021 | Kruger | G06F 3/016 |

OTHER PUBLICATIONS

Cheng et al. : "An Integrative Model of Respiratory and Cardiovascular Control in Sleep-Disordered Breathing"; Respiratory Physiology & Neurobiology, 174 (2010), pp. 4-28.

Lu et al.: "A Human Cardiopulmonary System Model Applied to the Analysis of the Valsalva Maneuver"; An J Physiol Heart Circ Physiol, 281:H2661-H2670, 2001.

* cited by examiner

ENHANCED ACUTE CARE MANAGEMENT COMBINING IMAGING AND PHYSIOLOGICAL MONITORING

CROSS-REFERENCE TO PRIOR APPLICATIONS

This application is the U.S. National Phase application under 35 U.S.C. § 371 of International Application No. PCT/IB2016/056025, filed on Oct. 7, 2016, which claims the benefit of U.S. Provisional Application Ser. No. 62/239,308, filed Oct. 9, 2015. These applications are hereby incorporated by reference herein, for all purposes.

FIELD

The following relates to the medical monitoring and therapy arts, respiratory, cardiovascular, and cardiopulmonary monitoring and therapy arts, medical ventilation arts, and related arts.

BACKGROUND

Physiological modeling of the cardiovascular, pulmonary, or other physiological system can be advantageous for patient monitoring of patients with cardiac, respiratory, or similar medical conditions, and for patient therapy such as patient ventilation. Mechanical ventilation (MV) is a commonly-used life-saving procedure, which is administered when a patient is not able to achieve adequate ventilation (and thereby gas exchange) by spontaneous breathing. In passive patient ventilation, the patient is unable to assist in breathing, and the ventilator operates in a pressure control mode in which the ventilator pressure performs the entire work of breathing. In active patient ventilation, the patient can at least assist in breathing, and the ventilator operates in a pressure support mode to provide sufficient pressure to overcome any deficiency in the patient's work of breathing (WoB). Volume control modes of ventilator operation are also known, in which flow rate or volume is the controlled parameter, rather than controlling pressure (although pressure limit settings may also be applied to guard against pulmonary barotrauma). While MV can be a life-saving therapy, improper ventilation can harm the patient, for example producing lung-damaging oxygen toxicity or ventilator-induced lung injury (VILI) at high applied pressure.

Patient monitoring is a key to providing effective therapy. Monitored vital signs (i.e. variables) such as heart rate, respiration rate, carbon dioxide readings via capnography, and so forth enable medical personnel to assess the health and function of the cardiopulmonary system. However, many relevant metrics of cardiopulmonary health cannot be directly measured, for example cardiac output, or can only be measured at discrete times with high latency, e.g. arterial blood gases (ABG) monitored by periodic laboratory testing of drawn arterial blood samples. Such "hidden" metrics may in some cases be indirectly assessed by a physician using heuristic rules or the like, but these are approximate and require skilled medical analysis.

Physiological modeling, for example of the cardiovascular and/or pulmonary system, can provide a tool for directly and continuously, monitoring such otherwise "hidden" metrics. A physiological model takes as inputs measured vital signs (e.g. heart rate, respiratory rate, capnography values), demographic information (e.g. age, gender). The physiological model fits parameterized equations to these inputs, with some fitted parameters being hidden metrics of interest such as cardiac output, ABG values, WoB, and so forth. To account for dynamic cardiopulmonary behavior, the physiological model preferably employs differential or other time-dependent equations. Some known cardiopulmonary (CP) models of this type are described in: Lu et al., "A human cardiopulmonary system model applied to the analysis of the valsalva maneuver", *Am J Physiol Heart Circ Physiol,* 281:H2661-H2679, 2001; Cheng et al., "An integrative model of respiratory and cardiovascular control in sleep-disordered breathing", *Respir Physiol Neurobiol,* 174: 4-28, 2010; and Chbat et al., "A Comprehensive Cardiopulmonary Simulation Model for the Analysis of Hypercapnic Respiratory Failure", $31^{st}$ Annual Intl Conf. of the IEEE EMBS (Minneapolis, Minn., USA, Sep. 2-6, 2009). Although there has been substantial success in developing increasingly accurate physiological models, especially for the cardiovascular, pulmonary, or combined cardiopulmonary system, further improvement in accuracy of these models for clinical applications would be beneficial.

The following provides new and improved systems and methods which overcome the foregoing problems and others.

BRIEF SUMMARY

In accordance with one aspect, a patient monitoring device includes at least one physiological sensor configured to acquire at least one measured value for a patient of at least one monitored physiological variable. A cardiovascular (CV), pulmonary, or cardiopulmonary (CP) modeling component includes a microprocessor programmed to: receive the measured values of the at least one monitored physiological variable; receive a value for at least one patient-specific medical image parameter generated from at least one medical image of the patient; compute values for the patient of unmonitored physiological variables based on the measured values for the patient of the monitored physiological variables and the patient-specific medical image parameter; and at least one of (1) display the computed values and (2) control a therapy device delivering therapy to the patient based on the computed values.

In accordance with another aspect, a non-transitory storage medium stores instructions readable and executable by one or more microprocessors to perform a patient monitoring method. Measured values for a patient of at least one monitored physiological variable are received from patient physiological sensors. A patient-specific value for a parameter is determined from a medical image of the patient. Values for the patient of unmonitored physiological variables are computed using a cardiovascular (CV), pulmonary, or cardiopulmonary (CP) model (40) with inputs including the measured values for the patient of the monitored physiological variables and with a model parameter of the CV, pulmonary, or CP model set to the patient-specific value determined for the parameter from the medical image of the patient.

One advantage resides in providing more accurate continuous, real-time values for unmeasured physiological variables and/or for physiological variables with high measurement latency (e.g. due to measurement via laboratory tests).

Another advantage resides in providing clinical cardiovascular, pulmonary, or cardiopulmonary modeling with reduced reliance upon averaged or other approximate model parameter values.

Another advantage resides in providing a mechanical ventilator system or other therapy system with an improved control via more accurate physiological modeling.

Another advantage resides in providing clinical cardiovascular, pulmonary, or cardiopulmonary modeling with reduced computational complexity as model parameter values obtained from medical images are held fixed during iterative model optimization.

Further advantages of the present invention will be appreciated to those of ordinary skill in the art upon reading and understand the following detailed description. It will be appreciated that any given embodiment may achieve none, one, more, or all of the foregoing advantages and/or may achieve other advantages.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

A problem recognized herein with physiological models employed in a clinical setting is that certain underlying patient parameters may be poorly characterized. For example, it is common to assume default values for critical anatomical dimensions such as cardiac vessel cross-sections or tissue elasticity (or corresponding functional parameters such as blood flow resistance, tissue compliance or so forth). These assumed values may be weak approximations for some patients whose individual physiology deviates strongly in a relevant aspect from the average. In improvements disclosed herein, an imaging modality such as ultrasound imaging is employed to directly measure one or more model parameters, thereby improving model accuracy and consequently improving the accuracy of variables output by the model. The improved clinical modeling finds numerous applications in cardiac and respiratory clinical practice. In illustrative examples, such models are used to monitor a patient who is receiving mechanical ventilation, and optionally also to control the mechanical ventilator. However, it will be appreciated that the disclosed improved cardiovascular, pulmonary, or cardiopulmonary monitoring will find diverse applications in cardiac and respiratory clinical practice, such as in assessing or predicting organ failure (e.g. heart failure, acute respiratory distress syndrome (ARDS), monitoring respirator wean-off or so forth.

Figure 1:
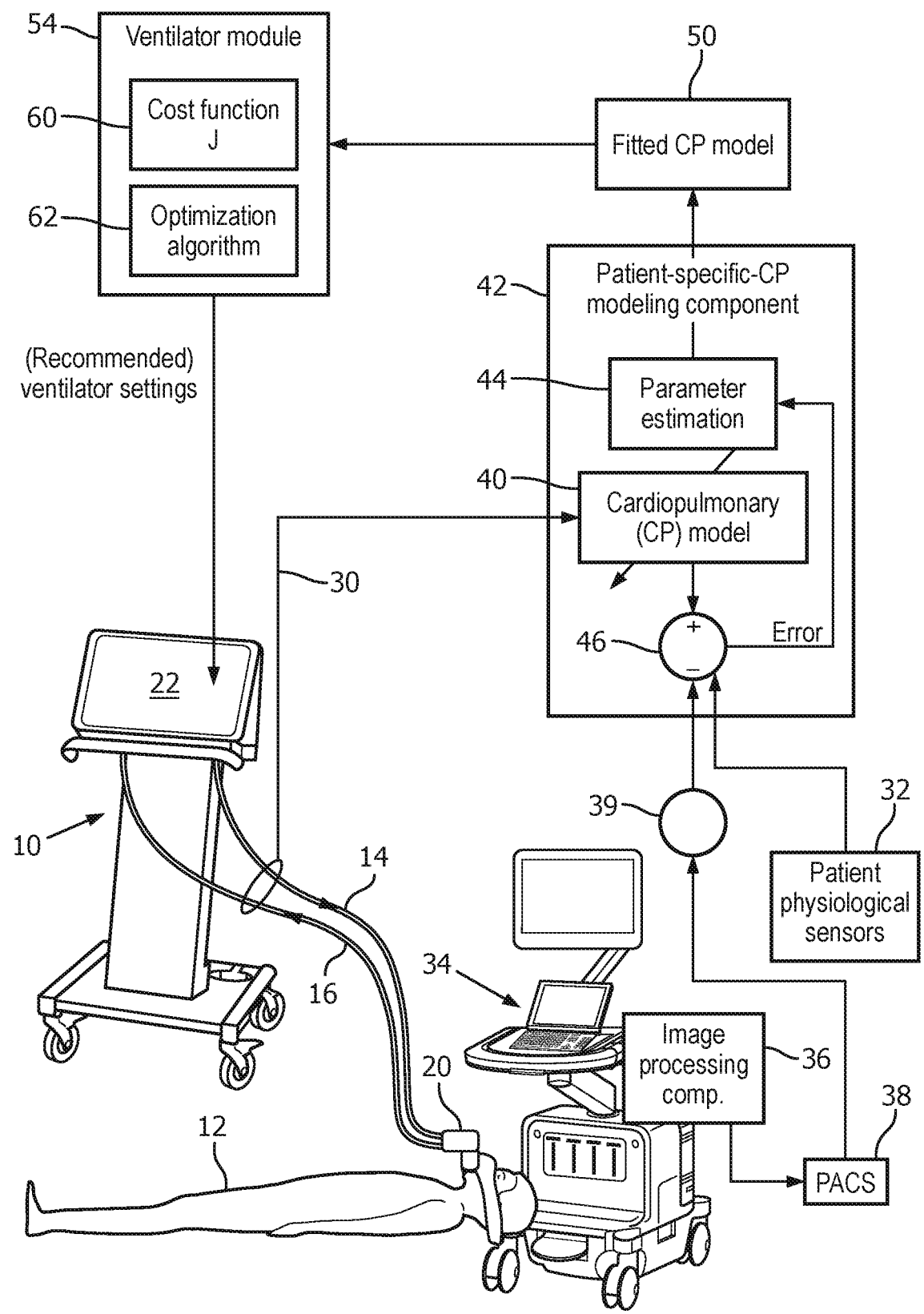
FIG. 1 diagrammatically shows a medical ventilation system.

With reference to FIG. 1, an illustrative patient monitoring device is used to monitor a patient receiving mechanical ventilation via a mechanical ventilator 10 that delivers air flow in accordance with ventilator settings to a ventilated patient 12 via an inlet air hose 14. Exhaled air returns to the ventilator 10 via an exhalation air hose 16. A Y-piece or T-piece 20 (or alternatively a tracheal tube) couples air from the discharge end of the inlet air hose 14 to the ventilated patient 12 during inhalation and couples exhaled air from the ventilated patient 12 into the exhalation air hose 16 during exhalation. Not shown in FIG. 1 are numerous other ancillary components that may be provided depending upon the ventilation mode and other therapy being received by the ventilated patient 12. Such ancillary components may include, by way of illustration: an oxygen bottle or other medical-grade oxygen source for delivering a controlled level of oxygen to the air flow, usually controlled by a Fraction of Inspired Oxygen ($FiO_2$) ventilator setting; a humidifier plumbed into the inlet line 14; a nasogastric tube to provide the patient 12 with nourishment; and so forth. The mechanical ventilator 10 has a user interface including, in the illustrative example, a touch-sensitive display component 22 via which the physician, respiratory specialist, or other medical personnel can enter or adjust the ventilator settings and monitor measured physiological variables and operating parameters of the mechanical ventilator 10. Additionally or alternatively, the user interface may include physical user input controls (buttons, dials, switches, et cetera), a keyboard, a mouse, audible alarm device(s), indicator light(s), or so forth.

FIG. 1 diagrammatically illustrates a system for monitoring the ventilated patient 12. The patient monitoring device receives as inputs ventilator output information 30, either directly measured or known from the ventilator settings, such as a controlled pressure and/or controlled air flow applied to the air way via Y-piece 20. These measurements use built-in monitoring devices of the mechanical ventilation system, such as an airway flow meter, airway pressure meter, a capnograph measuring respired carbon dioxide ($CO_2$) levels, or so forth. The patient monitoring device further receives as input measured values for the ventilated patient 12 of physiological variables that are monitored by patient physiological sensors 32. These sensors 32 may include, by way of illustration, a heart rate monitor, blood pressure monitor (e.g. arterial blood pressure, central venous pressure, et cetera), an oxygen saturation sensor (e.g. a pulse oximeter measuring heart rate and $SpO_2$ level), and so forth. Other physiological variables may be measured via laboratory tests performed on drawn tissue samples, e.g. blood tests. These physiological variables have high latency, by which it is meant that the value for such a variable reflects patient state at the time the blood or tissue sample was drawn, which may be several tens of minutes to several hours ago or longer.

FIG. 1 also shows an imaging device 34 configured to obtain at least one medical image of the ventilated patient 12. The imaging device 34 can be any suitable imaging system, such as x-ray, ultrasound, magnetic resonance (MR), computed tomography (CT), positron emission tomography (PET), single photon emission computer tomography (SPECT), and the like. The illustrative imaging device 34 is an ultrasound imaging system 34, which has advantages for routine patient monitoring due to its high degree of portability enabling some ultrasound procedures to be carried out in the patient's hospital room. The ultrasound imaging system 34 is commonly used to perform various diagnostic tasks for a patient suffering from a cardiac or respiratory ailment. For example, the ultrasound imaging system 34 may be used to perform angiography, which combines B-mode imaging and Doppler blood flow measurement to diagnose and monitor vascular disease. The ultrasound imaging system 34 may additionally or alternatively be used to perform echocardiography to assess cardiac disease, and/or to detect tracheal lesions or perform pulmonary congestion via analysis of B-line reverberation artifacts. The imaging system 34 typically includes an image processing component 36 which may be integral with the imaging system itself (e.g. implemented on a controller or other microprocessor of the imaging system 34) or may be implemented on a different system such as a desktop or notebook computer operatively connected with the imaging system 34. The medical images acquired by the imaging system 34, and additional information produced by post-acquisition image processing performed by the image processing component 36, are suitably stored in a Picture Archiving and Communication System (PACS) 38 in Digital Imaging and Communications (DICOM) format, or another storage system and/or other storage format.

In addition, as disclosed herein medical images from the illustrative ultrasound 34, and/or from another medical imaging system such as CT, MR, or PET, are used to determine the patient-specific value of at least one parameter of the ventilated patient 12 that is used in physiological modelling. To this end, images can be taken of the patient 12 to determine physiological parameter values for a tissue, organ, or vessel, such as size, cross-sectional-area, volume, shear modulus, relative Young's modulus, skin turgor, percentage of myocardium ischemia, mean or instantaneous velocity, flow rate, flow profile, cardiac ejection fraction, cardiac output, amount of mitral valvular regurgitation, movement, boundary, and the like. For example, an image can be taken of the aorta of the patient 12 to determine the diameter thereof.

Figure 2:
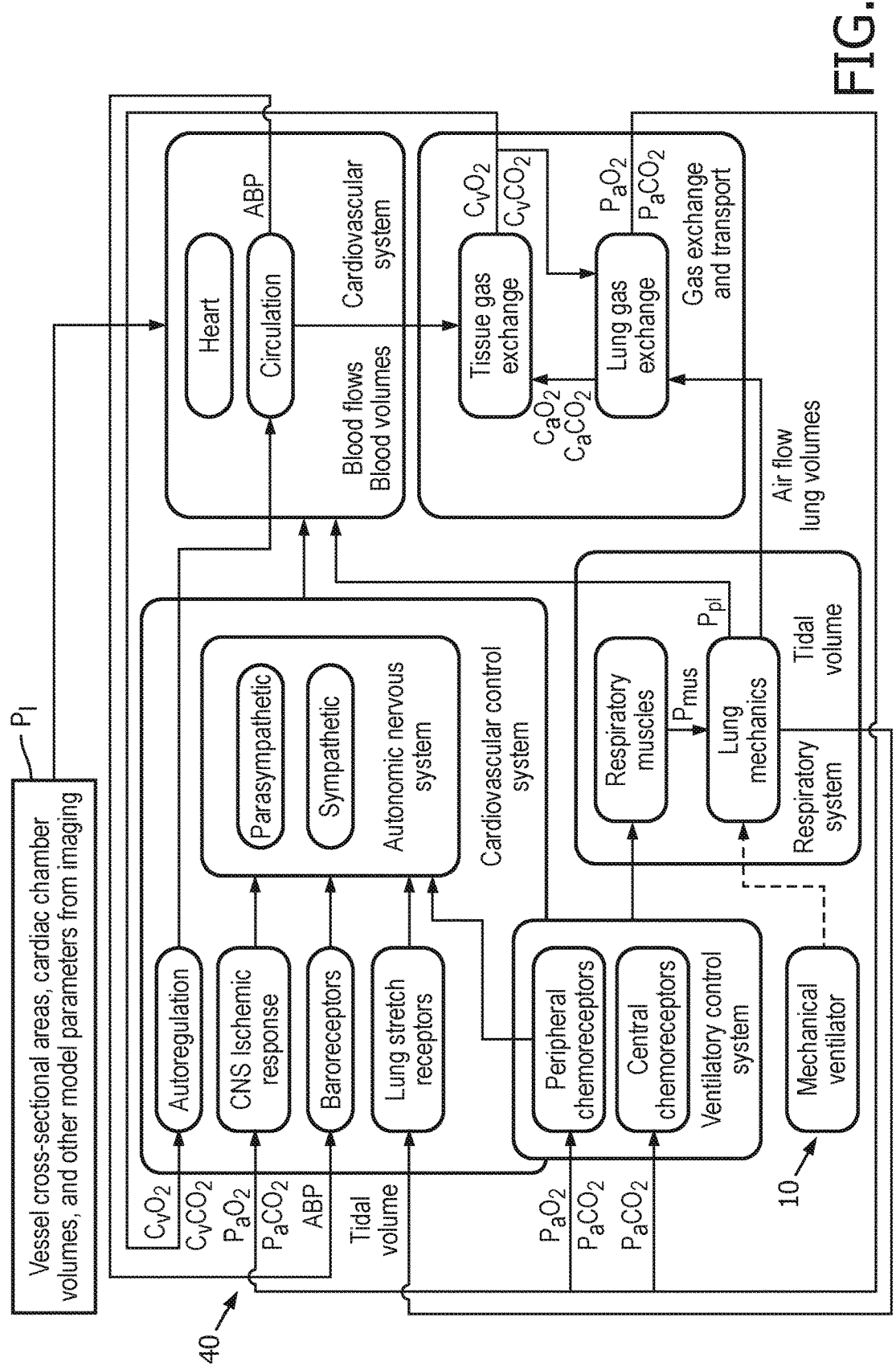
FIG. 2 diagrammatically shows a cardiopulmonary model used by the medical ventilation system of FIG. 1.

The measured values of physiological variables from the sensors 32 and from the ventilator 10 (if available) provide substantial information about the physical state of the patient 12. However, other physiological variables of interest are not directly measurable, such as cardiac output; or are only measurable via laboratory testing with high latency. To provide real-time values for such variables, a physiological model 40 is provided. The illustrative physiological model is a cardiopulmonary (CP) model 40 which models the cardiovascular system and the respiratory system including interactions between these two systems. FIG. 2 diagrammatically shows a suitable block diagram of the CP model 40. The CP model 40 models various physiological features, such as cardiovascular circulation, respiratory mechanics, tissue and alveolar gas exchange, short-term neural control mechanisms acting on the cardiovascular and/or respiratory functions, or so forth, as shown in detail in FIG. 2. The illustrative model 40 is a cardiopulmonary model that models both cardiovascular and pulmonary systems and their interactions. However, in other embodiments only one or the other of these systems may be modeled, e.g. the model may also be a cardiovascular (CV) model or a pulmonary model. To account for dynamic physiological behavior, the physiological model 40 preferably employs differential or other time-dependent equations. Various physiological models of the cardiovascular and/or pulmonary systems can be employed as the model 40. Some suitable models are described, for example, in: Lu et al., "A human cardiopulmonary system model applied to the analysis of the valsalva maneuver", *Am J Physiol Heart Circ Physiol,* 281:H2661-H2679, 2001; Cheng et al., "An integrative model of respiratory and cardiovascular control in sleep-disordered breathing", *Respir Physiol Neurobiol,* 174:4-28, 2010; and Chbat et al., "A Comprehensive Cardiopulmonary Simulation Model for the Analysis of Hypercapnic Respiratory Failure", 31$^{st}$ Annual Intl Conf of the IEEE EMBS (Minneapolis, Minn., USA, Sep. 2-6, 2009). In the illustrative case of a ventilated patient, the model 40 optionally includes aspects simulating the mechanical ventilator 10 (i.e. a ventilator model aspect), for example a controlled pressure applied to the airway by the mechanical ventilator 10 via the Y-piece 20 and inlet hose 14 can be modeled as an external ventilator pressure source applied to a resistance representing the larynx (see Chbat et al, supra), while a controlled air flow applied to the airway by the ventilator 10 can be similarly modeled as an external flow source. Each physiological variable measured by the sensors 32, or by built-in sensors of the mechanical ventilator system 10, has a measured value associated with it, as described in more detail below. The illustrative ventilated patient CP model 40 provides a substantial advantage, in that it can be used to generate computed values for the ventilated patient 12 of unmonitored physiological variables (that is, physiological variables that are not directly monitored by the sensors 32 or obtained from the images generated by the imaging device 34) based on the values measured by the sensors 32 for the ventilated patient 12 of the monitored physiological variables, and also based on the ventilator settings since these are also inputs to the ventilated patient CP model 40. Another advantage of the ventilated patient CP model 40 is that it can predict patient response to changes in the ventilator settings, as the ventilated patient CP model 40 models interrelationships between the ventilator settings and the various physiological parameters.

The physiological model 40 also has various parameters representing organs, tissue, or the like. For example, in modeling the cardiovascular system the hydraulic impedance of various major cardiac vessels such as the aorta or inferior vena cava (IVC) are model parameters, and are typically computed from the lumen diameter (i.e. inner diameter) of the vessel (e.g. aorta) being modeled. More generally, some illustrative model parameters include: cardiac chamber volumes in the systolic and diastolic phases; percentage of cardiac ischemia; major vessel lumen diameters; tissue compliances measured in terms of shear modulus, Young's modulus, or so forth; cardiac blood flow parameters such as cardiac ejection fraction, cardiac output, or mitral valvular regurgitation; anatomical structure or tissue displacements such as movement of organ boundaries during cardiac and/or respiratory cycling; blood flow parameters such as blood velocity and/or volume in major vessels; lung volume; tracheal air flow; and so forth. In a common approach, "average" or "typical" values for these model parameters are employed; however, such a value may be in substantial error if the particular patient 12 has an atypical value for that parameter. Atypical values may, for example, result from medical conditions such as vascular stenosis (leading to reduced blood flow); cardiac problems leading to low ejection fraction and/or low cardiac output; lung congestion leading to low effective lung volume; and so forth. As recognized herein, precisely these types of atypical parameter values are likely to arise in a clinical setting in the case of a patient suffering from a cardiac and/or respiratory ailment.

As disclosed herein, patient-specific model parameter values are obtained by directly measuring the model parameters from medical images acquired using the illustrative ultrasound imaging system 34 or another available imaging system. In some clinical settings, such measurements may be generated by already-prescribed imaging sessions for tasks such as angiography, echocardiography, or lung ultrasound for assessment of pulmonary congestion, or may be generated by additional image processing performed on these images. In other clinical settings, a dedicated imaging session may be performed along with dedicated image processing to acquire the model parameters.

Referring back to FIG. 1, the imaging system 34 includes an image processing component 36 that processes images or imaging data from the imaging system 34 to generate various patient information. The image processing component 36 is programmed to determine one or more model parameters of the physiological model 40. In some cases the image processing component 36 may produce the model parameter value as part of some other analysis (e.g. angiography, echocardiography). In other cases, the image processing component is modified versus a conventional ultrasound system designed to perform a task such as angiography or echocardiography, where the modification includes an additional processing module that produces the physiological model parameter. For example, the image processing component 36 may display an ultrasound image of the heart and request that the physician indicate the aorta lumen diameter by marking opposite inner-diameter sidewalls of the aorta using a mouse pointer. Blood flow velocity may be determined from Doppler ultrasound data.

A model parameter determined from the medical image(s) is imported to a patient-specific physiological modeling component 42 (for example, embodied by a computer, a processor of the mechanical ventilator 10, a processor of the ultrasound system 34, or so forth) either manually or, preferably, automatically via an electronic link 39. In one example, the electronic link 39 is via the Picture Archiving and Communication system (PACS) 38. This link 39 may be configured as a "push"-type link in which the image processing component 36 of the imaging system 34 notifies the physiological modeling component 42 of availability of the parameter on the PACS 38; or as a "pull"-type link in which the physiological modeling component 42 periodically checks the PACS 38 for updated model parameters. Moreover, it will be appreciated that communication via the PACS 38 is an illustrative example, and other communication pathways are contemplated such as transfer via a direct connection (e.g. over WiFi) between the two components 36, 42. It is also contemplated to employ manual transfer, for example by programming the modeling component 42 to include a configuration file editing window via which a user can input patient-specific values for certain model parameters, and the imaging system 34 displays the parameter value on its display so that the user can read the parameter value from the imaging system 34 and then enter it into the configuration window of the modeling component 42.

With continuing reference to FIG. 1, in the illustrative example the ventilated patient CP model 40 is personalized in real-time by the patient-specific CP modelling component 42 to fit the specific ventilated patient 12. The ventilated CP model 40 receives: (i) the measured values of the at least one monitored physiological variable from the sensors 32 and/or from built-in sensors of the ventilator 10; and (ii) receives the values for one or more physiological model parameters generated from a medical image of the patient from the imaging device 34, 36. A parameter estimation algorithm 44 is applied to adapt the CP model to the patient's changing conditions based on physiological variable measurements collected from the patient 12 by the sensors 32 and the one or more physiological parameters determined from the medical images obtained from the imaging device 34. A comparator component 46 determines the error between (1) predictions of the ventilated patient CP model 40 for the monitored physiological variables; and (2) the values for the ventilated patient 12 of the monitored physiological variables as measured by the sensors 32. The criterion used in the parameter estimation routine 44 is the minimization of this error. In performing this optimization, model parameters may in general be treated as adjustable variables whose values are optimized as part of the parameter estimation 44, or may be held fixed. However, the one or more model parameters obtained from the imaging system 34 are preferably held fixed at the value(s) determined from the medical images during the estimation 44, which reduces computational complexity and also reduces the likelihood of substantial error due to the specific patient 12 having an atypical parameter value due to some condition such as vascular stenosis or a cardiac or pulmonary ailment. By way of illustration, in FIG. 2 parameter values $P_I$ from medical images, such as vessel cross-sectional areas, cardiac chamber volumes, and/or so forth are provided to the cardiovascular component of the CP model 40. The output of the patient-specific CP modelling component 42 is a fitted ventilated patient CP model 50 that may be used to output values for unmeasured physiological variables and/or for physiological variables with high latency (e.g. laboratory test values). The CP model 50 may additionally or alternatively be used by a ventilator module 54 to optimize ventilator settings of the mechanical ventilator 10, as described in more detail below.

The parameter estimation routine 44 can compute values for the patient of unmonitored physiological variables based on the measured values for the patient of the monitored physiological variables. Some examples of unmonitored physiological variables that can be calculated by the parameter estimation routine 44 include lung compliance, upper airway resistance, and aortic stenosis. While the parameter estimation routine 44 could calculate most, if not all, of the physiological parameters and variables based on the monitored physiological variable values obtained by the sensors 32, using images from the imaging device 34 to obtain one or more physiological model parameters advantageously reduces the number of calculations for the parameter estimation routine 44 to perform (i.e, the number of values to optimize is reduced). This enhances the accuracy of the model 40, while reducing the "diminishing returns" thereof after performing numerous calculations. It will be appreciated that since imaging is usually performed in discrete imaging sessions, the imaging-based variables would be updated each time the patient 12 undergoes an ultrasound imaging session. In practice, such updating may already be performed in order to accommodate real-time changes in measured physiological variables. Depending upon medical condition and practice of the medical institution, such imaging sessions may already be routinely scheduled for diagnostic and/or monitoring purposes, so that no additional imaging procedures would need to be performed.

In some embodiments, the CP model 50 is used to provide close-loop feedback control of the illustrative mechanical ventilator 10, or alternatively to provide ventilator setting recommendations. In the illustrative example of FIG. 1, the ventilator module 54 uses the fitted ventilated patient CP model 50 to compute a cost function 60 for adjustment of the ventilator settings, and applies an optimization algorithm 62 (e.g. a space search, or a more complex optimization such as gradient descent) to identify an optimal ventilator settings. More particularly, the ventilator module 54 uses the fitted ventilated patient CP model 50 to predict a patient response to an adjustment to compute the value of the cost function 60 for the fitted ventilated patient CP model. The cost function 60 represents an aggregate cost associated with each adjustment. (Note that "cost" as used herein also encompasses benefit, e.g. the cost function 60 may be constructed so that a ventilator system adjustment predicted to actually the aggregate condition of the ventilated patient 12 produces a low cost, or even a negative cost depending upon the cost function design). The cost function 60 may be defined by aggregating cost terms such as arterial $O_2$ and $CO_2$ blood content goals, avoiding oxygen toxicity, obtaining a target alveolar pressure, and so forth. The optimization performed by the optimization algorithm 62 may be a constrained optimization in which the optimization is constrained by one or more constraints specified by the physician or other medical personnel. For example, one such constraint may require that arterial blood oxygen partial pressure ($PaO_2$) lie within a physician-specified range, and/or that the arterial blood carbon dioxide partial pressure ($PaCO_2$) lie within a physician-specified range.

The various data processing components 36, 42, 54 are suitably implemented as a microprocessor programmed by firmware or software to perform the disclosed operations. In some embodiments, the microprocessor is integral to the mechanical ventilator 10 and/or to the imaging system 34, so that the data processing is directly performed by the ventilator 10 and/or imaging system 34. In other embodiments the microprocessor is separate from the mechanical ventilator 10, for example being the microprocessor of a desktop computer. The various data processing components 36, 42, 54 of the ventilator settings optimization system may also be implemented as a non-transitory storage medium storing instructions readable and executable by a microprocessor (e.g. as described above) to implement the disclosed operations. The non-transitory storage medium may, for example, comprise a read-only memory (ROM), programmable read-only memory (PROM), flash memory, or other repository of firmware for the ventilator 10. Additionally or alternatively, the non-transitory storage medium may comprise a computer hard drive (suitable for computer-implemented embodiments), an optical disk (e.g. for installation on such a computer), a network server data storage (e.g. RAID array) from which the ventilator 10 or a computer can download the system software or firmware via the Internet or another electronic data network, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A patient monitoring device, comprising:
at least one physiological sensor configured to acquire at least one measured value for a patient of at least one monitored physiological variable; and
a cardiovascular (CV), pulmonary, or cardiopulmonary (CP) modeling component comprising a microprocessor programmed to:
receive the at least one measured value of the at least one monitored physiological variable;
receive ventilator output information including ventilator settings of a mechanical ventilator configured to be connected with the patient to provide ventilation to the patient in accordance with the ventilator settings and/or values measured by the mechanical ventilator;
receive a value for at least one patient-specific medical image parameter generated from at least one medical image of the patient, the at least one patient-specific medical image parameter including at least one anatomic structural measurement generated from the at least one medical image of the patient;
compute values for the patient of unmonitored physiological variables based on the at least one measured value for the patient of the monitored physiological variables, the ventilator output information, and the at least one patient-specific medical image parameter using a cardiovascular (CV), pulmonary, or cardiopulmonary (CP) model; and
at least one of display the computed values and control the mechanical ventilator to provide ventilation to the patient in accordance with the ventilator settings controlled at least in part based on the computed values.

2. The device according to claim 1, wherein the at least one anatomic structural measurement generated from the at least one medical image of the patient includes one or more of a size of the anatomical structure, a cross-sectional-area of the anatomical structure, a volume of the anatomical structure, and percentage of myocardium ischemia.

3. The device according to claim 1, wherein the at least one patient-specific medical image parameter includes at least one anatomic structure or tissue elasticity, compliance, resistance, shear modulus, Young's modulus, or skin turgor measurement generated from the at least one medical image of the patient.

4. The device according to claim 1, wherein the at least one patient-specific medical image parameter includes at least one blood flow measurement generated from the at least one medical image of the patient; and wherein the at least one blood flow measurement includes one or more of mean instantaneous velocity, flow rate, flow profile, cardiac ejection fraction, cardiac output, or amount of mitral valvular regurgitation.

5. The device according to claim 1, further comprising:
an image processing component comprising at least one processor programmed to:
receive at least one medical image of the patient;
generate the value for the at least one patient-specific medical image parameter from the received at least one medical image of the patient; and
communicate the generated value to the CV, pulmonary, or CP modeling component via an electronic link.

6. The device according to claim 5, wherein the electronic link comprises:
a Picture Archiving and Communication System (PACS) in which the image processing component is programmed to store the at least one medical image and the generated value;
wherein the CV, pulmonary, or CP modeling component is programmed to read the generated value from the PACS.

7. The device according to claim 6, wherein the CV, pulmonary, or CP modeling component is programmed to automatically detect the updated value for the at least one patient-specific medical image parameter and re-compute the values for the patient of unmonitored physiological variables using the updated value.

8. The device according to claim 1, wherein the CV, pulmonary, or CP model is a pulmonary or CP model, the at least one patient-specific medical image parameter includes at least one of diaphragm motion determined from an ultrasound image of the patient and lung size determined from an x-ray or computed tomography image of the patient, and the computed values for the patient of unmonitored physiological variables include one or more of tidal volume, minute ventilation, and dead space volume.

9. The device according to claim 1, wherein the CV, pulmonary, or CP model is a CV or CP model, the at least one patient-specific medical image parameter characterizes blood flow in the inferior vena cava determined from an ultrasound image of the patient, the monitored physiological variables include an arterial blood pressure value, and the computed values for the patient of unmonitored physiological variables include cardiac output.

10. A non-transitory computer readable medium having computer executable instructions stored thereupon, that, when executed by one or more microprocessors, causes the one or more microprocessors to perform a patient monitoring method comprising:
receiving at least one measured value for a patient of at least one monitored physiological variable from at least one physiological sensor;
receiving ventilator output information including ventilator settings of a mechanical ventilator configured to be connected with the patient to provide ventilation to the patient in accordance with the ventilator settings and/or values measured by the mechanical ventilator;
determining a value for at least one patient-specific medical image parameter from at least one medical image of the patient; and
computing values for the patient of unmonitored physiological variables based on the at least one measured value for the patient of the monitored physiological variables, the ventilator output information, and the at least one patient-specific medical image parameter using a cardiovascular (CV), pulmonary, or cardiopulmonary (CP) model; and
at least one of displaying the computed values on a display component and controlling the mechanical ventilator to deliver ventilation to the patient in accordance with ventilator settings controlled at least in part based on the computed values.

11. The non-transitory computer readable medium of claim 10, wherein the at least one patient-specific medical image parameter is a cardiac parameter selected from the group consisting of percentage of myocardium ischemia, cardiac ejection fraction, cardiac output, and amount of mitral valvular regurgitation.

12. The non-transitory computer readable medium of claim 10, wherein the at least one patient-specific medical image parameter is an anatomical structure or tissue parameter selected from the group consisting of shear modulus, relative Young's modulus, skin turgor, movement, and boundary position.

13. The non-transitory computer readable medium of claim 10, wherein the patient monitoring method further comprises:
repeating the determining and computing operations in response to the at least one medical image of the patient being updated by a more recently acquired medical image of the patient.

14. The non-transitory computer readable medium of claim 10, wherein the CV, pulmonary, or CP model is a pulmonary or CP model, the at least one patient-specific medical image parameter includes at least one of diaphragm motion determined from an ultrasound image of the patient and lung size determined from an x-ray or computed tomography image of the patient, and the computed values for the patient of unmonitored physiological variables include one or more of tidal volume, minute ventilation, and dead space volume.

15. The non-transitory computer readable medium of claim 10, wherein the CV, pulmonary, or CP model is a CV or CP model, the at least one patient-specific medical image parameter characterizes blood flow in the inferior vena cava determined from an ultrasound image of the patient, the monitored physiological variables include an arterial blood pressure value, and the computed values for the patient of unmonitored physiological variables include cardiac output.

16. The non-transitory computer readable medium of claim 10, wherein the at least one patient-specific medical image parameter includes at least one anatomic structural measurement generated from the at least one medical image of the patient, and wherein the at least one anatomic structural measurement includes one or more of a size of the anatomical structure, a cross-sectional-area of the anatomical structure, a volume of the anatomical structure, and percentage of myocardium ischemia.

* * * * *